US012605405B2

(12) United States Patent
Wehling et al.

(10) Patent No.: US 12,605,405 B2
(45) Date of Patent: Apr. 21, 2026

(54) METHODS FOR THE PRODUCTION OF PHARMACEUTICAL AGENTS

(71) Applicant: ORTHOGEN AG, Düsseldorf (DE)

(72) Inventors: Peter Wehling, Düsseldorf (DE); Julio Reinecke, Cologne (DE); Julia Heindirk, Korschenbroich (DE)

(73) Assignee: ORTHOGEN AG, Düsseldorf (DE)

( * ) Notice: Subject to any disclaimer, the term of this patent is extended or adjusted under 35 U.S.C. 154(b) by 1265 days.

(21) Appl. No.: 17/269,659

(22) PCT Filed: Aug. 22, 2019

(86) PCT No.: PCT/EP2019/072468
§ 371 (c)(1),
(2) Date: Feb. 19, 2021

(87) PCT Pub. No.: WO2020/039026
PCT Pub. Date: Feb. 27, 2020

(65) Prior Publication Data
US 2021/0260110 A1 Aug. 26, 2021

(30) Foreign Application Priority Data

Aug. 23, 2018 (EP) .................................... 18190367

(51) Int. Cl.

| | |
|---|---|
| *G01N 33/53* | (2006.01) |
| *A61K 8/36* | (2006.01) |
| *A61K 8/64* | (2006.01) |
| *A61K 8/98* | (2006.01) |
| *A61K 9/00* | (2006.01) |
| *A61K 31/202* | (2006.01) |
| *A61K 35/14* | (2015.01) |
| *A61K 38/17* | (2006.01) |
| *A61K 38/20* | (2006.01) |
| *A61K 38/21* | (2006.01) |
| *B01L 3/00* | (2006.01) |

(52) U.S. Cl.
CPC .............. *A61K 35/14* (2013.01); *A61K 8/361* (2013.01); *A61K 8/64* (2013.01); *A61K 8/983* (2013.01); *A61K 9/0019* (2013.01); *A61K 31/202* (2013.01); *A61K 38/1709* (2013.01); *A61K 38/2006* (2013.01); *A61K 38/217* (2013.01); *B01L 3/508* (2013.01)

(58) Field of Classification Search
None
See application file for complete search history.

(56) References Cited

U.S. PATENT DOCUMENTS

| | | | |
|---|---|---|---|
| 3,706,305 A | 12/1972 | Berger et al. | |
| 2009/0047242 A1* | 2/2009 | Reinecke ................ A61P 37/00 424/529 | |

FOREIGN PATENT DOCUMENTS

| | | | | |
|---|---|---|---|---|
| DE | 10 2012 019088 A1 | 4/2014 | | |
| EP | 0 899 271 A1 | 3/1999 | | |
| EP | 2 156 841 A1 | 2/2010 | | |
| EP | 2769745 B1 * | 5/2016 | .......... | A61M 1/0209 |
| WO | 00/46249 A1 | 8/2000 | | |
| WO | 2004/103439 A1 | 12/2004 | | |
| WO | 2006/007529 A2 | 1/2006 | | |
| WO | 2007/090569 A1 | 8/2007 | | |
| WO | 2017/080668 A1 | 5/2017 | | |
| WO | 2018/033227 A1 | 2/2018 | | |
| WO | 2018/033227 A8 | 2/2018 | | |
| WO | 2018033226 A1 | 2/2018 | | |

OTHER PUBLICATIONS

Peter Wehling et al., "Autologous Conditioned Serum in the Treatment of Orthopedic Diseases", The Orthokine® Therapy, Biodrugs, 2007, 21 (5): 323-332, 11 pages.
International search report for PCT/EP2019/072468, dated Nov. 12, 2019.
Office Action issued Feb. 29, 2024 in Chinese Application No. 201980069941.1.
Communication dated May 4, 2023 issued by the European Patent Office in application No. 19759529.1.
Communication dated Apr. 4, 2023 issued by the Japanese Patent Office in application No. 2021-510088.
Communication dated Apr. 2, 2025, issued in European Application No. 19 759 529.1.
Communication dated Oct. 31, 2024 in Chinese Application No. 201980069941.1.

* cited by examiner

*Primary Examiner* — Michael D Pak
(74) *Attorney, Agent, or Firm* — Sughrue Mion, PLLC

(57) ABSTRACT

The invention relates a method for producing a pharmaceutical composition, comprising the steps of: providing a liquid collected from a mammal, which liquid comprises cellular constituents of blood, providing a container having an internal surface, contacting said liquid with said internal surface, incubating said liquid contacted with said internal surface for an incubation time, wherein said liquid is agitated with an agitation means at least once during said incubation time, and after said incubation time has passed, obtaining said pharmaceutical composition by steps comprising (1) collecting said liquid or (2) removing part of or the entirety of said cellular constituents from said liquid and collecting the remainder.

15 Claims, 5 Drawing Sheets

METHODS FOR THE PRODUCTION OF PHARMACEUTICAL AGENTS

CROSS-REFERENCE TO RELATED APPLICATIONS

This application is a National Stage of International Application No. PCT/EP2019/072468 filed Aug. 22, 2019, which claims priority under U.S.C. § 119(a) to European Patent Application No. 18190367.5 filed on Aug. 23, 2018.

Conditioned serum (CS) is a biologic pharmaceutical composition produced from conditioned peripheral whole blood. Autologous conditioned serum (ACS) is CS that is administered to the same person who was the donor of the blood. CS has anti-inflammatory and possibly chondropro-tective properties. The therapy with CS (ACS) relies on cytokines and other factors formed upon conditioning of blood, i.e. its incubation in contact with a surface, which leads to the accumulation of certain factors. This is normally done in the presence of glass beads. ACS has been used since the 1990s, originally mainly in osteoarthritis and other orthopaedic diseases such as rheumatoid arthritis and (de-generative) spinal disorders, where it has shown a beneficial effect on symptoms and disease progression. Usually, blood from a patient is drawn into a pyrogen-free syringe contain-ing glass beads to initiate the activation of cells, in particular leukocytes such as monocytes. After incubation, the blood is recovered and cells are removed by centrifugation. The resulting serum is enriched for anti-inflammatory cytokines such as Interleukin (IL)-1 receptor antagonist (IL-1Ra), IL-4, IL-10 and IL-13 as well as several growth factors, including insulin-like growth factor-1, platelet-derived growth factor, and transforming growth factor-31, and returned to the same patient, e.g. into the affected region such as by intra-articular injection. IL-1Ra is a naturally occurring inhibitor of the cytokine IL-1. IL-1 is thought to be an important mediator of inflammation, pain and tissue destruction.

In the onset of orthopaedic diseases, biomechanical fac-tors play a role. In pathogenesis, additionally the activation of a whole cascade of cytokines is important. A pivotal process is the local release of cytokines that effect the destruction of hyaline cartilage. This leads to additional production of pro-inflammatory and destructive factors and thus further hyaline cartilage destruction. Since IL-1B is a key mediator of many inflammatory and degenerative dis-eases, therapeutic strategies focus on counteracting its bio-logical activities. Agents that inhibit the action of IL-1B have a high therapeutic potential. Various approaches are the administration of e.g. IL-1Ra, soluble forms of IL-1 recep-tors and anti-inflammatory cytokines such as IL-4, IL-10, and IL-13, which inhibit the synthesis of IL-1, increase the synthesis of IL-1Ra, or both. IL-1Ra inhibits IL-1B com-petitively and has affinity to type I and II IL-1 receptors. Recombinant IL-1Ra is approved by the U.S. FDA for the treatment of rheumatoid arthritis. It is hypothesised that the local IL-1Ra concentration is too low in degenerative dis-eases to inhibit the destruction of cartilage, muscles, spine tissue, and other joint structures.

ACS is a drug that may alter the course of osteoarthritis development (DMOAD) and thereby possibly delay or even prevent the need for surgical interventions, such as total joint replacement. ACS has shown clinical benefits in osteoar-thritis such as knee osteoarthritis, temporomandibular joint osteoarthritis, hip osteoarthritis and coxarthrosis and a decrease of bone tunnel widening after anterior cruciate ligament reconstructive surgery. The injection of ACS into affected tissue has also shown clinical effectiveness and safety in animal models and studies, as well as in human clinical studies, for the treatment of lumbar stenosis, disc prolapse and muscle injuries. It has potential in many inflammatory conditions, such as nerve inflammation. Therefore, it is a useful non-operative technique to reduce pain, inhibit tissue degradation and support tissue restora-tion.

Evidence has accumulated that not only IL-1Ra, but also additional factors may be involved in clinical efficacy of CS (ACS). The ratio of IL-1Ra to IL-1, which should be at least 10:1, preferably at least 100:1, is also useful as a quality control parameter for conditioned blood. It is hypothesised that the clinical and preclinical effects of ACS may be attributed to a synergistic action of multiple factors present in it. Effects may partially result from the activation of endogenous wound healing mechanisms by exposure of blood cells to alien surfaces, inducing mechanisms such as the coagulation cascade and tissue repair. The long-term effects in osteoarthritis (which extend e.g. over for example two years) may tentatively be explained by re-establishing a healthy joint homeostasis. Due to the autologous nature of ACS, the risk/benefit ratio is excellent and no side effects have to be expected.

It is known that whole blood, and conditioned whole blood, contains exosomes. Exosomes are small vesicles, which cells secrete into their environment. For example biological liquids such as serum, urine, saliva, peritoneal liquid, cerebrospinal liquid and synovial liquid contain exosomes. CS also contains exosomes. Most types of cells that have been investigated are able to secrete exosomes. Secretion occurs through release through/from the cell's plasma membrane. Depending on the cell type in which they are generated, exosomes contain inter alia a variable com-bination of proteins. Methods for the preparation and admin-istration of exosomes are described for example in WO 2006/007529 A2.

Taken together, ACS, exosomes from ACS and/or exo-some-free preparations obtained from ACS are known in one or more of the following: the treatment of ageing or in the use as an anti-ageing agent (WO 2018/033227 A1), in the treatment of an ageing-related disorder (WO 2017/080668 A1) or for use by injection into the skin (WO 2018/033226 A1), in the treatment of one or more selected from muscle diseases, tendon diseases, food intolerance, drug intoler-ance, diseases involving the immune system, psoriasis, chronic wounds such as diabetic ulcers, neurodermatitis, inflammation and irritation of the nervous system, endo-metriosis, chronic eye inflammation in horses (WO 2007/ 090569 A1), rheumatism, osteoarthritis, joint conditions and diseases, dorsal pain (e.g. with a neurological cause), neuro-orthopaedic conditions, conditions of a nerve root, condi-tions of an intervertebral disc, orthopaedic conditions (WO 00/46249 A1), lumbar radicular pain, juvenile rheumatoid arthritis, rheumatoid arthritis, juvenile Morbus Still and allergy (WO 2006/007529 A2). ACS is also in widespread use for equine osteoarthritis, where it considerably improves clinical lameness and may protect cartilage from degrada-tion.

Common specific disorders correlated with age are ath-erosclerosis, cardiovascular disease, cancer, hearing deficits, vision deficits, cataracts, retinal degeneration, e.g. macular degeneration, osteoporosis, type 2 diabetes, hypertension, liver failure, cachexia, kyphosis, gait disorders, tremors, ataxia, dystonia, reduced grip strength, muscle wasting and hair greying. Age also promotes neurodegeneration and similar disorders, such as mild cognitive impairment, Alzheimer's disease, cerebrovascular disease, Parkinson's disease and amyotrophic lateral sclerosis.

In spite of the successes achieved so far, there remains a need for new pharmacologic treatments of the aforementioned and other disorders.

It is the problem of the present invention to provide novel methods for the production of pharmaceutical agents. Preferably, the produced pharmaceutical agents are improved over the pharmaceutical agents of the prior art, for example with respect to the level of active substances or the ratio of desired factors to other factors (such as undesired ones). Advantageously the pharmaceutical agents that can be produced according to the present invention are one or more of: fast to produce, easy to produce, cost effective and highly body compatible.

The above statements, and any description of exemplified embodiments herein, do not constitute any waiver of certain embodiments or features.

This problem is solved by a method for producing a pharmaceutical composition, comprising the steps of:

(a) providing a liquid collected from a mammal, which liquid comprises cellular constituents of blood, (b) providing a container having an internal surface, (c) contacting said liquid with said internal surface, (d) incubating said liquid contacted with said internal surface for an incubation time, wherein said liquid is agitated with an agitation means at least once during said incubation time, and (e) after said incubation time has passed, obtaining said pharmaceutical composition by steps comprising (1) collecting said liquid or (2) removing part of or the entirety of said cellular constituents from said liquid and collecting the remainder.

In the following, this method is also referred to as "the method of the present invention".

A preferred "mammal" is a farm animal (such as a cow), a sport animal (such as a horse or a camel), a pet (such as a cat or a dog) or a primate. The most preferred mammal is a human being.

A "cellular constituent of blood" means any cellular constituent of whole blood, whether present in large or small amounts. Preferred cellular constituents of blood are leukocytes (in particular neutrophils, eosinophils, basophils, lymphocytes, B cells, T cells, NK cells, dendritic cells or monocytes). Particularly preferred cellular constituents of blood are monocytes.

Preferably the "liquid" is a blood sample. In an particularly preferred embodiment the liquid is a blood sample which is (i) a whole blood sample or (ii) a whole blood sample from which certain cells have been depleted (partially, substantially completely or completely). In this context, the cells that have been depleted are preferably selected from erythrocytes, leukocytes (in particular neutrophils, eosinophils, basophils, lymphocytes, B cells, T cells, NK cells, dendritic cells and/or monocytes) and platelets. More preferably the cells that have been depleted are erythrocytes (being cells that lack a nucleus and thus gene expression ability), in which case the liquid preferably comprises platelets and white blood cells. In case the liquid is a whole blood sample from which erythrocytes have been depleted, it is preferred to choose alternative (1) in step (e) of the method of the present invention, that is to obtain the pharmaceutical composition by collecting said liquid after the incubation time has passed. Alternatively, a method is preferred wherein said cellular constituents of blood comprise platelets and step (e) is a step of, after said incubation time has passed, obtaining said pharmaceutical composition by degranulating said platelets by adding calcium ions and/or thrombin, and thereafter collecting said liquid. As an alternative to degranulating, platelets may be lysed.

The "internal surface" of the container refers to the internal surface of the container itself. In particular, the surface of any particles that might be contained in the container (macroscopic particles, microscopic particles and/or nanoparticles).

It is unnecessary to, and preferred not to, add any external stimulators or activators. Before the providing step, the method of the present invention additionally includes the step of collecting said liquid (preferably blood sample, more preferably whole blood sample) from said mammal.

Where embodiments of the present invention are described as "containing" or "comprising" certain subject matter, e.g. methods steps, constituents or other features, it is understood that preferred embodiments consist of said subject matter, except where the context dictates otherwise.

It is understood that "treatment" also includes prophylaxis.

"Disorders" as used herein refers to disturbances in normal function or appearance and includes diseases, complications and conditions.

Upon incubation in contact with a surface (conditioning), the cellular constituents of blood are responsible for the formation and accumulation of cytokines, exosomes and other factors. These factors induced in the liquid, and their combination, have a pharmaceutical effect. Therefore the formed composition is a pharmaceutical composition. This composition may be used in pharmacologic treatment. Before that, cells may be removed from the composition, although this is not mandatory. The term "exosomes" preferably additionally comprises other extracellular vesicles (EV). Conditioning, as described above, leads to additional formation of exosomes.

It has now surprisingly been found that, when producing a pharmaceutical composition by incubating a liquid collected from a mammal comprising cellular constituents of blood in contact with an internal surface of a container, an agitation during incubation leads to differential changes in the contents of the composition, as compared to static incubation (i.e., in the absence of agitation). For example, a number of desired factors are induced more strongly or more rapidly than undesired ones, which may lead to more favourable ratio of desired factors to other factors. Therefore, the effect of agitation is a specific effect, which is an unexpected finding. The level of active substances (in particular desired factors) may be increased.

Thus, a novel and alternative method for the production of pharmaceutical agents is provided, which leads to agents different from the agents of the prior art. The method makes it possible to produce pharmaceutical agents that are improved over the prior art with respect to the level of active substances, the ratio of desired to other factors (such as undesired ones), or otherwise. Thus, new pharmacological treatments become available for the above or other disorders. It is even possible to avoid potential problems in the prior art resulting from an unfavourable ratio of desired to other factors or too low a level of active substances.

In some embodiments it is conceivable to shorten the incubation time, because a pharmaceutical composition with the desired properties (such as a certain level of active substances) may be formed more rapidly. Thus, certain embodiments of the method of the present invention may be advantageous in that the pharmaceutical composition is fast to produce. It is possible to select easy and off-the-shelf devices and components to carry out the method of the present invention. Consequently, it is possible to produce the pharmaceutical compositions in an easy and/or cost effective way. Due to the use of materials collected from a mammal, it is possible to produce a pharmaceutical composition having high body compatibility, because it is possible to avoid ingredients that are foreign to the body.

For example if the liquid is a whole blood sample, the pharmaceutical composition resulting from the method of the present invention is a certain type of conditioned whole blood. If, for instance, the entirety of cellular constituents is removed from the conditioned whole blood, the remainder is a certain type of conditioned serum (preferably a certain type of autologous conditioned serum). Since, as compared to static incubation, agitation leads to changes in the contents of the composition, these agents are different from the agents of the prior art.

In a preferred method of the present invention, in said pharmaceutical composition the concentration of exosomes is higher than in the absence of agitation under otherwise identical conditions, preferably at least 1.1-fold, 1.2-fold, 1.3-fold, 1.4-fold, 1.5-fold, 1.6-fold, 1.7-fold, 1.8-fold, 1.9-fold or in particular at least 2-fold as high, the concentration of gelsolin is higher than in the absence of agitation under otherwise identical conditions, preferably at least 1.1-fold, 1.2-fold, or in particular at least 1.3-fold as high, the concentration of resolvin is higher than in the absence of agitation under otherwise identical conditions, preferably at least 1.1-fold as high the concentration of IL-1Ra is higher than in the absence of agitation under otherwise identical conditions, preferably at least 1.1-fold, 1.2-fold, or in particular at least 1.3-fold as high, at least one ratio of the concentrations of an anti-inflammatory mediator (preferably IL-1Ra) and an inflammatory mediator (preferably IL-1B) is higher than in the absence of agitation under otherwise identical conditions, preferably at least 1.1-fold, 1.2-fold, 1.3-fold, 1.4-fold, 1.5-fold, 1.6-fold, 1.7-fold, 1.8-fold, 1.9-fold or in particular at least 2-fold as high, or at least one concentration of an inflammatory mediator (preferably IL-5 or IFN-γ) is essentially the same as before said incubation.

In another aspect, the present invention relates to a pharmaceutical composition produced by the method of the present invention (in particular in one of the preferred embodiments as described herein). Below, this pharmaceutical composition is also called "the pharmaceutical composition of the present invention".

Since the cellular constituents of blood secrete exosomes, the pharmaceutical composition of the present invention contains exosomes. As mentioned above, exosomes have therapeutic efficacy.

The average diameter of the exosomes, as established by means of a transmission electron microscope, is preferably between 30 and 200 nm, in particular between 50 and 190 nm, between 70 and 180 nm, between 90 and 160 nm or between 100 and 150 nm. Exosomes of this size are the basis for an especially high efficacy, larger vesicle sizes may be indicative of conglomerates that contain damaged exosomes and aggregates. However, larger exosomes may also be functional. This applies to exosomes with a diameter range of 200 to 5000 nm or 100 to 800 nm. These larger exosomes may be obtained by differential centrifugation.

A further aspect of the present invention relates to a method for producing exosomes, comprising producing a pharmaceutical composition by the method of the present invention (in particular in one of the preferred embodiments as described herein) and collecting exosomes contained in the pharmaceutical composition. This method is also referred to as "the exosome production method of the present invention".

Therefore, in another aspect, the present invention relates to exosomes produced by the exosome production method of the present invention (in particular in one of the preferred embodiments as described herein). These exosomes are also referred to as "the exosomes of the present invention".

Collecting may be by concentrating or isolating the exosomes, which may for example be realised through centrifugation at 2,000 to 1,000,000 g, 10,000 to 800,000 g, 20,000 to 600,000 g, 50,000 to 400,000 g, 80,000 to 200,000 g and in particular 100,000 g, as such accelerations are especially suitable to concentrate or isolate exosomes, depending on their sizes. Such a centrifugation is preferably conducted for at least 10 min, for at least 30 min, especially for at least 60 min. The pellet formed by the centrifugation then contains the exosomes. Preferably the concentrated or isolated exosomes are then taken up in a fluid (preferably a buffered solution such as PBS, or alternatively e.g. plasma or serum). Optionally they are then filtrated, for example through a 0.2 μm filter.

Also exosome-free preparations have therapeutic efficacy. An additional aspect of the present invention thus relates to a method for producing an exosome-free preparation, comprising producing a pharmaceutical composition by the method of the present invention (in particular in one of the preferred embodiments as described herein) and removing the exosomes contained in the pharmaceutical composition from the pharmaceutical composition, thereby obtaining said exosome-free preparation. Herein, this method is also called "the exosome-free preparation production method of the present invention".

In yet another aspect, the present invention relates to an exosome-free preparation produced by the exosome-free preparation production method of the present invention (in particular in one of the preferred embodiments as described herein). This preparation is also referred to as "the exosome-free preparation of the present invention".

The composition of the present invention, the exosomes of the present invention and/or the exosome-free preparation of the present invention preferably contain cytokines and/or growth factors.

A further aspect of the present invention relates to a method for producing a combination, comprising producing (i) a pharmaceutical composition by the method of the present invention (ii) exosomes by the exosome production method of the present invention or (iii) an exosome-free preparation by the exosome-free preparation production method of the present invention, and combining said pharmaceutical composition, exosomes and exosome-free preparation, respectively, with a means for storage thereof, a means for application thereof to a mammal or an excipient. This method is also referred to as "the combination production method of the present invention".

The means for storage is not the same as the above container. A preferred means for storage is selected from a vial, a plurality of vials, an ampoule, a plurality of ampoules, a bottle, a plurality of bottles, a medical liquid bag and a plurality of medical liquid bags.

A preferred means for application to a mammal is selected from a syringe and a plurality of syringes.

Examples of an excipient are a carrier, a diluent, a vehicle, a preservative, a stabiliser, an isotonic agent and a solvent.

A preferred excipient is selected from saline (preferably a sodium chloride solution, in particular a 0.9% sodium chloride solution) and a buffer (preferably a phosphate buffer).

Another aspect relates to a combination produced by the combination production method of the present invention (in particular in one of the preferred embodiments as described herein). This combination is also called "the combination of the present invention".

Additionally, the present invention relates to a kit comprising:

a container having an internal surface for being contacted with a liquid collected from a mammal, which liquid comprises cellular constituents of blood, an agitation means for agitating said liquid at least once during an incubation time in which said liquid is incubated in contact with said internal surface and preferably a means for application of a pharmaceutical composition to a mammal, wherein said pharmaceutical composition is obtained by removing part of or the entirety of said cellular constituents from said liquid and collecting the remainder after said incubation time.

Herein, this kit is also called "the kit of the present invention".

Further, the present invention relates to the use of the pharmaceutical composition of the present invention, the exosomes of the present invention, the exosome-free preparation of the present invention, the combination of the present invention or the kit of the present invention as a cosmetic product.

Yet another aspect of the present invention relates to the use of a container or an agitation means in the method of the present invention (in particular in one of the preferred embodiments as described herein).

The present invention also relates to the pharmaceutical composition of the present invention, the exosomes of the present invention, the exosome-free preparation of the present invention, the combination of the present invention or the kit of the present invention for use as a medicament. Although this use may be by application to a different mammal than that from which said liquid has been collected, it is preferably by application to the same mammal from which said liquid has been collected, i.e. the treatment is preferably autologous (especially for reasons of safety). Preferably, the use is in combination with one or more other effective agents.

A further aspect of the present invention is the pharmaceutical composition of the present invention, the exosomes of the present invention, the exosome-free preparation of the present invention, the combination of the present invention or the kit of the present invention for use in the treatment of a condition selected from an orthopaedic condition, a joint condition, a tendon condition, pain, a degenerative spinal disease (preferably a herniated disc), a condition of an intervertebral disc, a neuro-orthopaedic condition, a condition of a nerve root, irritation of the nervous system, inflammation of the nervous system, a neuropathic condition, a disease involving the immune system, an autoimmune disease, psoriasis, chronic wounds (preferably a diabetic ulcer), a muscle disease, food intolerance, drug intolerance, endometriosis, a condition in which apoptosis plays a role, ageing and an ageing-related disorder, for use as an anti-ageing agent or for use as a medicament by injection into the skin.

Alternative wordings of this aspect of the present invention are:

use of the pharmaceutical composition of the present invention, the exosomes of the present invention, the exosome-free preparation of the present invention, the combination of the present invention or the kit of the present invention for the manufacture of a medicament for the treatment of a condition selected from an orthopaedic condition, a joint condition, a tendon condition, pain, a degenerative spinal disease (preferably a herniated disc), a condition of an intervertebral disc, a neuro-orthopaedic condition, a condition of a nerve root, irritation of the nervous system, inflammation of the nervous system, a neuropathic condition, a disease involving the immune system, an autoimmune disease, psoriasis, chronic wounds (preferably a diabetic ulcer), a muscle disease, food intolerance, drug intolerance, endometriosis, a condition in which apoptosis plays a role, ageing and an ageing-related disorder, for use as an anti-ageing agent or for use as a medicament by injection into the skin, use of the pharmaceutical composition of the present invention, the exosomes of the present invention, the exosome-free preparation of the present invention, the combination of the present invention or the kit of the present invention in the treatment of a condition selected from an orthopaedic condition, a joint condition, a tendon condition, pain, a degenerative spinal disease (preferably a herniated disc), a condition of an intervertebral disc, a neuro-orthopaedic condition, a condition of a nerve root, irritation of the nervous system, inflammation of the nervous system, a neuropathic condition, a disease involving the immune system, an autoimmune disease, psoriasis, chronic wounds (preferably a diabetic ulcer), a muscle disease, food intolerance, drug intolerance, endometriosis, a condition in which apoptosis plays a role, ageing and an ageing-related disorder, as an anti-ageing agent or as a medicament by injection into the skin, a method for treating a patient in need of treatment of a condition selected from an orthopaedic condition, a joint condition, a tendon condition, pain, a degenerative spinal disease (preferably a herniated disc), a condition of an intervertebral disc, a neuro-orthopaedic condition, a condition of a nerve root, irritation of the nervous system, inflammation of the nervous system, a neuropathic condition, a disease involving the immune system, an autoimmune disease, psoriasis, chronic wounds (preferably a diabetic ulcer), a muscle disease, food intolerance, drug intolerance, endometriosis, a condition in which apoptosis plays a role, ageing and an ageing-related disorder, in need of treatment with an anti-ageing agent or in need of treatment by injection into the skin, comprising administering to said patient an effective amount of the pharmaceutical composition of the present invention, the exosomes of the present invention, the exosome-free preparation of the present invention, the combination of the present invention or the kit of the present invention, thereby treating said condition in said patient, treating said patient with an anti-ageing agent or treating said patient by injection into the skin, or a drug for treating a condition selected from an orthopaedic condition, a joint condition, a tendon condition, pain, a degenerative spinal disease (preferably a herniated disc), a condition of an intervertebral disc, a neuro-orthopaedic condition, a condition of a nerve root, irritation of the nervous system, inflammation of the nervous system, a neuropathic condition, a disease involving the immune system, an autoimmune disease, psoriasis, chronic wounds (preferably a diabetic ulcer), a muscle disease, food intolerance, drug intolerance, endometriosis, a condition in which apoptosis plays a role, ageing and an ageing-related disorder, for use as an anti-ageing agent or for use as a medicament by injection into the skin comprising the pharmaceutical composition of the present invention, the exosomes of the present invention, the exosome-free preparation of the present invention, the combination of the present invention or the kit of the present invention.

The following statements apply irrespectively of the wording of this aspect of the present invention.

A preferred joint condition is selected from osteoarthritis, arthritis, joint inflammation, inflammatory loss of cartilage and rheumatism. The osteoarthritis may be caused by excess strain, have congenital or traumatic causes or be the result of another disease such as an inflammation. The osteoarthritis is preferably an activated osteoarthritis or an inflammatory osteoarthritis. The osteoarthritis or arthritis may be present in any joint like for example knee joint, hip joint, ankle joint, shoulder joint, vertebral joint, finger joint, cubital joint, toe joints, temporomandibular joint and wrist joint. The arthritis may be an arthritis caused by an infection such as bacterial arthritis or an arthritis not caused by an infection such as rheumatoid arthritis, psoriatic arthritis or gouty arthritis. Preferred are rheumatoid arthritis, juvenile rheumatoid arthritis and juvenile Morbus Still. Particularly preferred joint conditions are osteoarthritis and rheumatoid arthritis.

A preferred pain selected from dorsal pain (preferably with a neurological cause), arthritic pain and lumbar radicular pain.

The disease involving the immune system is preferably chronic eye inflammation (in particular in horses) or allergy. In a preferred embodiment, the use is in the resolution of inflammation. In another preferred embodiment, the use is in the suppression of TNF-$\alpha$ expression.

The autoimmune disease is preferably an autoimmune disease of a joint such as Morbus Bechterew, rheumatoid arthritis and systemic lupus erythematodes. Other preferred autoimmune diseases are neurodermitis or alopecia areata.

The pharmaceutical composition of the present invention, the exosomes of the present invention and the exosome-free preparation of the present invention may be administered by intravenous, intramuscular, intraarticular, transcutaneous, subcutaneous, intranasal, peroral, perineural or intrathecal administration, or by local injection or instillation or a combination of any of these. They are preferably intended for local administration. Thus in preferred embodiments they are intended for injection, particularly injection into the body region to be treated, particularly into the affected joint, into the affected nerve root or into the affected disc or into the local environment thereof. The pharmaceutical composition is thus particularly intended for intraarticular and/or periradicular injection. Alternatively the pharmaceutical composition of the present invention, the exosomes of the present invention and the exosome-free preparation of the present invention may be formulated for topical administration, particularly as a cream or gel or for systemic administration, particularly oral administration in the form of tablets, capsules or pastilles. The type of administration depends inter alia on the disease to be treated. In local osteoarthritis or degenerative spinal disease, local administration is preferred. The pharmaceutical composition of the present invention, the exosomes of the present invention and the exosome-free preparation of the present invention are suitably formulated for the different types of administration in a manner known to the person skilled in the art. Thus a pharmaceutical composition suitable for injection preferably has the form of a solution or dispersion or also a dry form e.g. as a powder or lyophilisate, which must be dissolved in an appropriate solvent such as water before the injection.

A preferred embodiment of the use in the treatment of the above conditions, as an anti-ageing agent or as a medicament by injection into the skin is in combination therapy with one or more additional effective agents. The additional effective agent(s) may also be present in the pharmaceutical composition of the present invention, the exosomes of the present invention, the exosome-free preparation of the present invention, the combination of the present invention and the kit of the present invention, or the additional effective agent(s) may be present in a different composition which may be administered simultaneously or sequentially.

The agitation takes place after contacting the liquid with the internal surface. When said contacting is by filling the liquid into the container, this means that the agitation takes place after filling the liquid into the container.

In the method of the present invention the liquid is preferably agitated by agitating the container. Preferably by agitating the liquid, it is mixed.

The liquid is preferably (1) agitated during the entirety of said incubation time,
(2) agitated two or more times during said incubation time,
(3) agitated for a total of at least 5 minutes (preferably for a total of at least 10, 15, 30 or 45 minutes or 1, 2, 3, 4, 5 or 6 hours),
(4) agitated at a point in time that is later than 10 minutes (preferably more than 15 minutes, 30 minutes or 1 hour) after the beginning of said incubation time,
(5) not agitated during the first 10 minutes of the incubation time, or
(6) agitated by one or more selected from: rotating the container around an axis thereof, moving an axis of the container along a closed trajectory, shifting the container, tilting the container, inverting the container, shaking the container, rotating the liquid, shifting the liquid and stirring the liquid, wherein the agitation is preferably uniform.

Preferably, the above option (6) is combined with any of options (1) to (5).

It is preferred to combine rotating the container around an axis thereof with moving an axis of the container along a closed trajectory. It is particularly preferred to combine rotating the container around its longitudinal axis (preferably at 10 to 20 rpm, in particular 15 rpm) with moving the longitudinal axis of the container along a closed (preferably continuous, more preferably elliptical and most preferably circular) trajectory at an identical frequency.

Preferred embodiments of rotating the container around an axis thereof are: rotating the container around its longitudinal axis, rotating the container around an axis perpendicular to its longitudinal axis or both. The container is preferably rotated around an axis thereof at 1 to 30 rpm, 5 to 25 rpm, 10 to 20 rpm, and in particular 15 rpm. When the axis is the longitudinal axis, usually higher speeds may be chosen than when the axis is an axis perpendicular to the longitudinal axis. Particularly preferred is a rotation around the longitudinal axis at 10 to 20 rpm, in particular 15 rpm.

The axis of the container moved along the closed trajectory is preferably its longitudinal axis or an axis perpendicular to its longitudinal axis. Preferably the closed trajectory is continuous, more preferably elliptical and most preferably circular. The movement is preferably done at 10 to 200 repetitions per minute (more preferably 20 to 180, 40 to 160, 60 to 140 and 80 to 120 repetitions per minute). When the axis is the longitudinal axis, usually higher speeds may be chosen than when the axis is an axis perpendicular to the longitudinal axis. Alternatively, in case moving an axis of the container along a closed trajectory is combined with rotating the container around an axis thereof, the frequency of the former may be chosen identically to the frequency of the latter. The diameter of the closed trajectory (or, in case it has more than one diameter, the longest diameter thereof) preferably has a length of 0.1 to 20 cm, 0.2 to 10 cm or 0.3 to 5 cm.

Shifting refers to a translational motion. Repeated bidirectional shifting is preferred, preferably with 10 to 200 repetitions per minute (more preferably 20 to 180, 40 to 160, 60 to 140 and 80 to 120 repetitions per minute). The translational path preferably has a length of 0.1 to 20 cm, 0.2 to 10 cm or 0.3 to 5 cm).

Shaking the container is preferably done at 10 to 200 repetitions per minute (more preferably 20 to 180, 40 to 160, 60 to 140 and 80 to 120 repetitions per minute).

Said agitation means is preferably selected from a wheel-shaped or propeller-shaped device for rotating the container around an axis thereof (and preferably simultaneously moving an axis of the container along a closed, preferably continuous, more preferably elliptical and most preferably circular trajectory), wherein preferably the device has a rotation axis that is perpendicular to the direction of gravity or tilted by an angle of up to 90 degrees (in particular up to 80, 70, 60, 50, 45, 40, 35, 30, 25, 20, 15, 10 or 5 degrees), and a shaking device, which is preferably adapted to carry out a circular or translational motion (in particular with a translational path and diameter, respectively, of 0.1 to 20 cm, 0.2 to 10 cm or 0.3 to 5 cm).

In case the shaking device is adapted to carry out a circular motion, it is also a device for moving an axis of the container along a closed trajectory. In case the shaking device is adapted to carry out a translational motion, it is also a device for shifting the container. The shaking movement preferably takes place in a horizontal plane.

The agitation means is preferably adapted to move with the frequencies indicated above.

Incubation of the liquid (preferably blood sample, more preferably whole blood sample) is preferably carried out for an incubation time of 15 min to 24 hours, 1 hour to 6 hours, 1 hour to 5 hours, 1.5 hours to 24 hours, 2 hours to less than 24 hours, 2 hours to 5 hours, at least 3 hours, 3 hours to 5 hours, 3 hours to less than 24 hours, 3 hours to 20 hours, 3 hours to 16 hours, 4 hours to 12 hours, at least 5 hours, 5 hours to 10 hours, 5 hours to 7 hours, up to 6 hours, at least 6 hours or at least 7 hours. Alternatively, incubation is carried out for an incubation time after which a measurable change in a certain parameter has occurred with respect to the value before incubation and/or the normal value of that parameter (such as the concentration of a cytokine, the concentration of a cytokine antagonist, in particular IL-1Ra, the concentration of exosomes and/or the concentration of a growth factor). In certain embodiments, a longer duration of incubation may be preferred, such as more than 24 hours, e.g. 30 hours, 36 hours or longer.

The incubation is preferably carried out at a temperature of 0° C. to 45° C., in particular at temperatures of 10° C. to 43° C., 20° C. to 41° C., 30° C. to 40° C., 35° C. to 39° C., 36° C. to 38° C. or 37° C. These temperatures ensure best efficacy.

The incubation may be carried out in the absence or presence of an added anticoagulant (preferably selected from warfarin, acenocoumarol, phenprocoumon, phenindione, heparin, low molecular weight heparin, synthetic inhibitors of factor Xa and thrombin inhibitors, most preferably heparin). It is preferably carried out in the absence of added heparin, and more preferably in the absence of any added anticoagulant.

Efficacy is in particular advantageous when the relationship between said incubation time and said internal surface is in accordance with the following equation: $t=f*A$, wherein t designates the incubation time, A designates the internal surface and f is smaller than or equal to 0.5 h/cm$^2$. Preferably f is smaller than or equal to 0.45 h/cm$^2$, smaller than or equal to 0.4 h/cm$^2$, smaller than or equal to 0.35 h/cm$^2$, smaller than or equal to 0.3 h/cm$^2$, smaller than or equal to 0.25 h/cm$^2$, smaller than or equal to 0.24 h/cm$^2$, smaller than or equal to 0.23 h/cm$^2$, and in particular smaller than or equal to 0.22 h/cm$^2$. This is useful for ensuring that the pharmaceutical composition of the present invention, the exosomes of the present invention the exosome-free preparation of the present invention, the combination of the present invention and the kit of the present invention have no undesired inflammatory potential. Particularly preferred are values for f in the range of 0.04 to 0.25 h/cm$^2$, 0.05 to 0.24 h/cm$^2$, 0.06 to 0.23 h/cm$^2$ and in particular 0.07 to 0.22 h/cm$^2$, whereas in some instances ranges from 0.1 to 0.22 h/cm$^2$, 0.12 to 0.22 h/cm$^2$ or 0.14 to 0.22 h/cm$^2$ may also be used.

Preferred ranges for the internal surface are 10 to 300 cm$^2$, 15 to 200 cm$^2$, 20 to 150 cm$^2$, 25 to 140 cm$^2$, 30 to 130 cm$^2$, 35 to 120 cm$^2$ and in particular 40 to 110 cm$^2$.

The "container" in the method of the present invention may be the same as that in which said liquid has been collected, or a different one.

Suitable containers are for example hypodermic needles, syringes, tubes such as vacuum tubes or test tubes, microtiter plates, syringes and transfusion bags. The container may e.g. have a diameter of 0.4 to 5 cm, 0.9 to 4 cm or 1.4 to 3.5 cm, and/or a length of 3 to 30 cm, 5 to 20 cm, 7 to 15 cm or 8 to 12 cm. Preferably, the container is cylindrical. A preferred container has a volume of 1 ml to 1000 ml, 3 ml to 750 ml, 5 ml to 500 ml, 7 ml to 300 ml, 8 ml to 200 ml, 9 ml to 150 ml, 10 ml to 100 ml, 11 ml to 80 ml and in particular 12 ml to 70 ml, however it may also have a volume of 15 ml to 65 ml, 20 ml to 60 ml, 25 ml to 50 ml or 30 to 40 ml. Preferably the ratio of internal surface and volume is 0.01 to 10 cm$^2$/ml. Preferred volumes of the liquid (preferably blood sample) are 0.5 ml to 900 ml, 1 ml to 700 ml, 2 ml to 400 ml, 3 ml to 300 ml, 6 ml to 200 ml, 7 ml to 150 ml, 8 ml to 100 ml, 9 ml to 80 ml and in particular 10 ml to 60 ml, however it may also have a volume of 11 ml to 55 ml, 12 ml to 50 ml, 15 ml to 40 ml or 20 to 30 ml. Preferably the volume of the liquid is at least 5%, 10%, 15%, 20% or 25% smaller than the volume of the container.

The container preferably has an internal surface (for contacting the liquid, preferably blood sample, more preferably whole blood sample) that comprises a surface made of one or more selected from glass, plastic, corundum and quartz. Preferably the glass is borosilicate glass. A preferred plastic is selected from the group consisting of polystyrene, polycarbonate, polyethylene and polypropylene. Preferably the internal surface for contacting the liquid of a container creates a fully enclosed space. Preferred containers have one or more of the following characteristics: symmetrical about a plane, symmetrical about an axis and cylindrical.

According to a preferred embodiment the container contains particles for contacting said liquid, which are one or more selected from macroscopic particles, microscopic particles and nanoparticles. For the purposes of the present application, macroscopic particles are defined as particles that are visible when viewed with the naked eye, microscopic particles are defined as particles that are too small to be visible when viewed with the naked eye but are visible when viewed with a microscope, and nanoparticles are defined as particles that are too small to be visible when viewed with a microscope (and that are preferably larger than 1 nm). Such particles serve the purpose of enlarging the surface for contacting the liquid (blood sample) (e.g. by another 0.3 to 90 cm$^2$, 2 to 80 cm$^2$, 5 to 70 cm$^2$, 10 to 60 cm$^2$, 20 to 50 cm$^2$ or 30 to 40 cm$^2$) and can have the shape of beads, granulates, powder, gels or wool. Preferred materials are glass (preferably borosilicate glass), plastic, corundum, quartz, gold and clay mineral (e.g. kaolin). Especially preferred are glass beads (in particular borosilicate glass beads), which preferably have a diameter of 0.5 to 5 mm, 1.5 to 4.5 mm, 2.5 to 4 mm and in particular 3.5 mm. The surface of the particles can optionally be modified, for example by incubation with a caustic agent such as 50% v/v chromosulphuric acid with subsequent repeated rinsing. The surface of such particles is not considered when calculating the "internal surface" of the container in accordance with the above equation. When during the incubation the liquid (preferably blood sample, more preferably whole blood sample) is in contact with a larger surface, induction may be more efficient.

EXAMPLES

The following Examples show that according to the present invention, pharmaceutical agents can be produced that are superior as compared to the prior art in various respects.

Example 1: Differential Production of IL-1β and IL-1Ra Due to Agitation During Incubation, One Test Subject A pharmaceutical agent was produced by the method of the present invention as follows:

Peripheral whole blood was collected from a healthy male human being. Blood was drawn into pyrogen-free 10 ml plastic syringes (interior length: ca. 84.5 mm, interior diameter: ca. 14.3 mm, interior surface: ca. 4100 mm$^2$, interior volume: ca. 13500 mm$^3$) which were untreated except that they contained purified polished borosilicate glass beads having a diameter of 3.5 mm (EOTII syringes, Orthogen AG, Düsseldorf, Germany).

The syringes containing the samples were incubated for various incubation times at 37° C. in a Sanyo MCO-20AIC incubator (Japan) without addition of $CO_2$.

One part of the samples was incubated without agitation (static incubation).

Another part of the samples was agitated during incubation. Agitation was achieved by a propeller shaped device for rotating the container around an axis thereof and simultaneously moving an axis of the container along a circular trajectory (Thermo Scientific Tube Revolver, catalogue number 88881001, Thermo Fisher Scientific, Germany), which was set to 15 rpm.

The device has a rotation axis that was aligned perpendicularly to the direction of gravity. Thus, containers were rotated around their longitudinal axis at 15 rpm, combined with moving the longitudinal axis of the containers along a circular trajectory at an identical frequency. Herein, this motion is also referred to as "slow rotation".

After incubation, insoluble components were removed by centrifugation. The resulting conditioned serum was collected and examined by ELISA for IL-1Ra and IL-1β concentrations.

Figure 1:
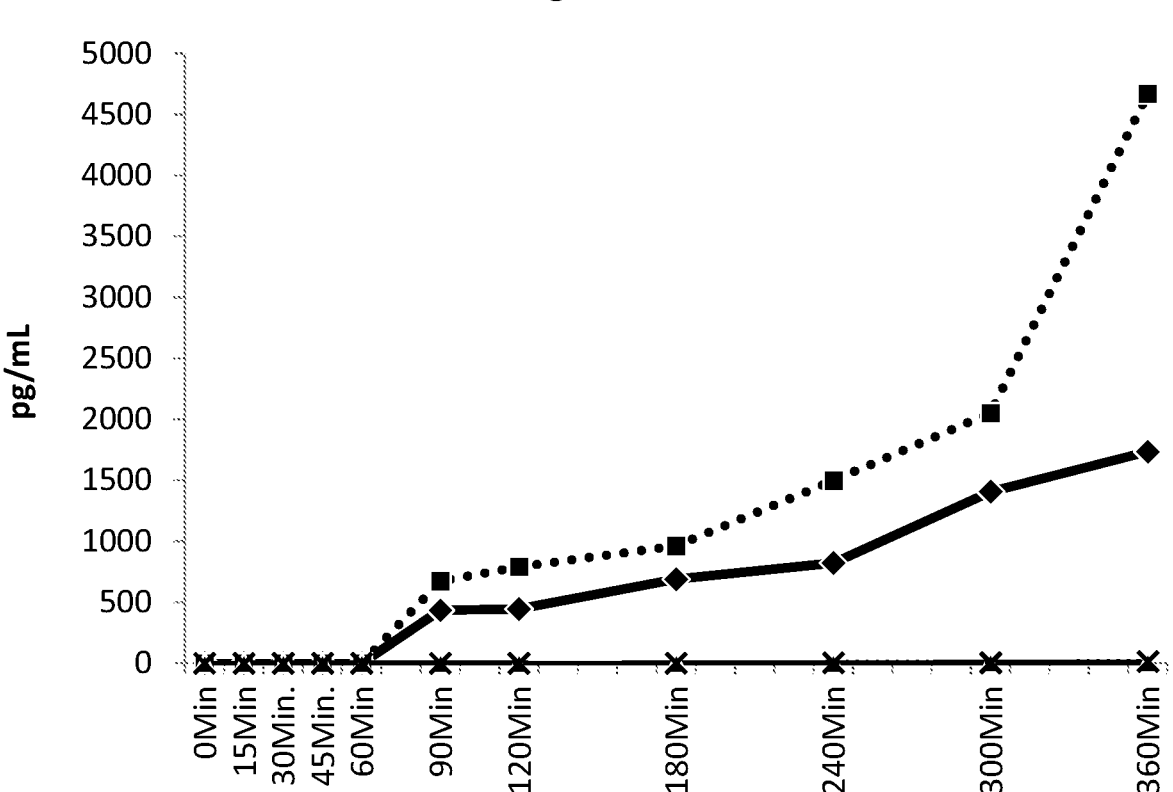
FIG. 1 shows the time course of the concentrations of IL-1B and IL-1Ra under two different conditions: static incubation and incubation with slow rotation (x-axis: time of incubation in minutes; y-axis: concentration of IL-1β and IL-1Ra, respectively, in pg/ml).

The results are shown in FIG. 1. Four curves are depicted, as explained in Table 1:

TABLE 1

| Curves shown in FIG. 1 | | |
| --- | --- | --- |
| | Static incubation | Incubation with slow rotation |
| IL-1Ra | diamond symbols, thick continuous line | square symbols, thick dotted line |
| IL-1β | triangle symbols, thin continuous line | X-shaped symbols, thin dotted line |

It can be seen that the concentrations of IL-1β remained negligible both when the incubation was static and when the incubation was performed with slow rotation. However, slow rotation led to a pronounced increase in IL-1Ra concentrations over time, as compared to static incubation. Therefore, agitation, in particular slow rotation, improves the level of the desired factor IL-1Ra without affecting the level of the undesired factor IL-1β.

Example 2: Differential Production of IL-1β and IL-1Ra Due to Agitation During Incubation, Four Test Subjects As mentioned above, IL-1 (e.g. IL-1β) is a mediator of inflammation, pain and tissue destruction. IL-1Ra is a naturally occurring inhibitor thereof and an important anti-inflammatory cytokine.

A pharmaceutical agent was produced by the method of the present invention as follows: Peripheral whole blood was collected from four healthy human beings. Blood was drawn into glass beads-containing syringes as described in Example 1.

The syringes containing the samples were incubated for various incubation times at 37° C. in a Sanyo MCO-20AIC incubator (Japan) without addition of $CO_2$.

One part of the samples was incubated without agitation (static incubation).

Another part of the samples was agitated during incubation with a shaking device carrying out a circular motion with a diameter of 3 mm (IKA MTS 4 shaker, IKA-Werke, Staufen, Germany) at 100 rpm. The syringes were fixed in a horizontal position in plastic plates attached to the shaker. Shaking was done in a horizontal plane. Thus, an axis of the container perpendicular to its longitudinal axis was moved along as circular trajectory at 100 repetitions per minute. The diameter of the closed circular trajectory (the diameter of the respective circle) was therefore 0.3 cm. Herein, this motion is also referred to as "fast shaking".

Yet another part of the samples was agitated during incubation by slow rotation as defined in Example 1.

After incubation, insoluble components were removed by centrifugation. The resulting conditioned serum was collected and examined by ELISA for IL-1Ra and IL-1β concentrations.

Figure 2:
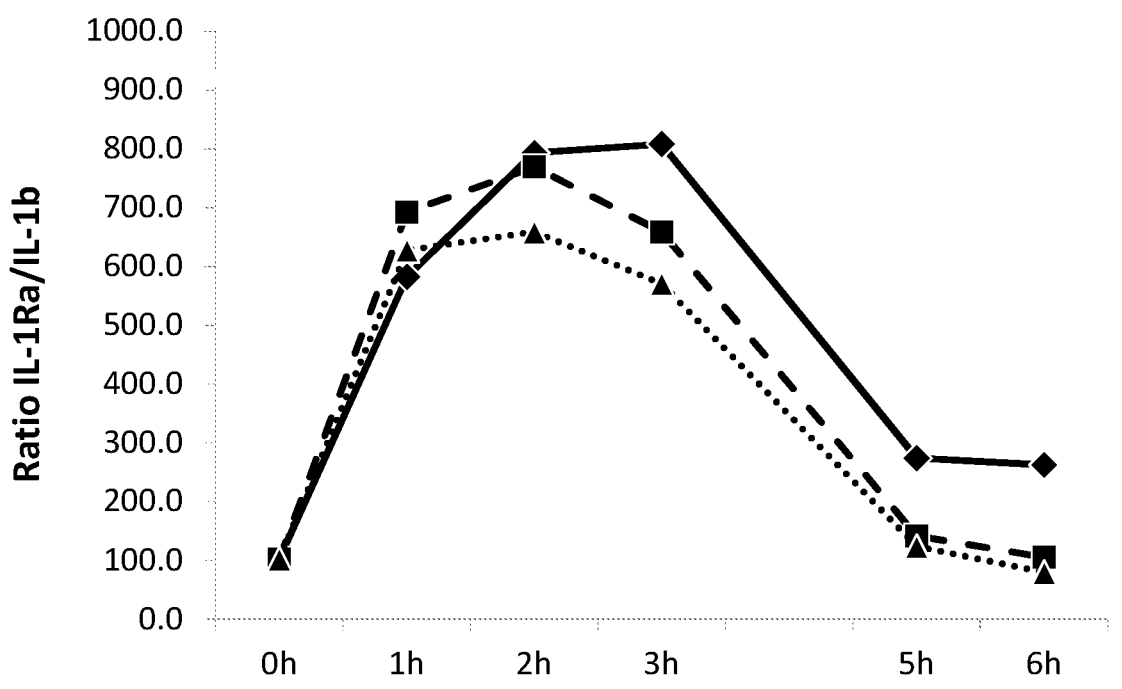
FIG. 2 shows the time course of the concentration ratio of IL-1Ra to IL-1β under three different conditions (x-axis: time of incubation in hours; y-axis: ratio of the concentrations of IL-1Ra and IL-1β, both in pg/ml).
Figure 3:
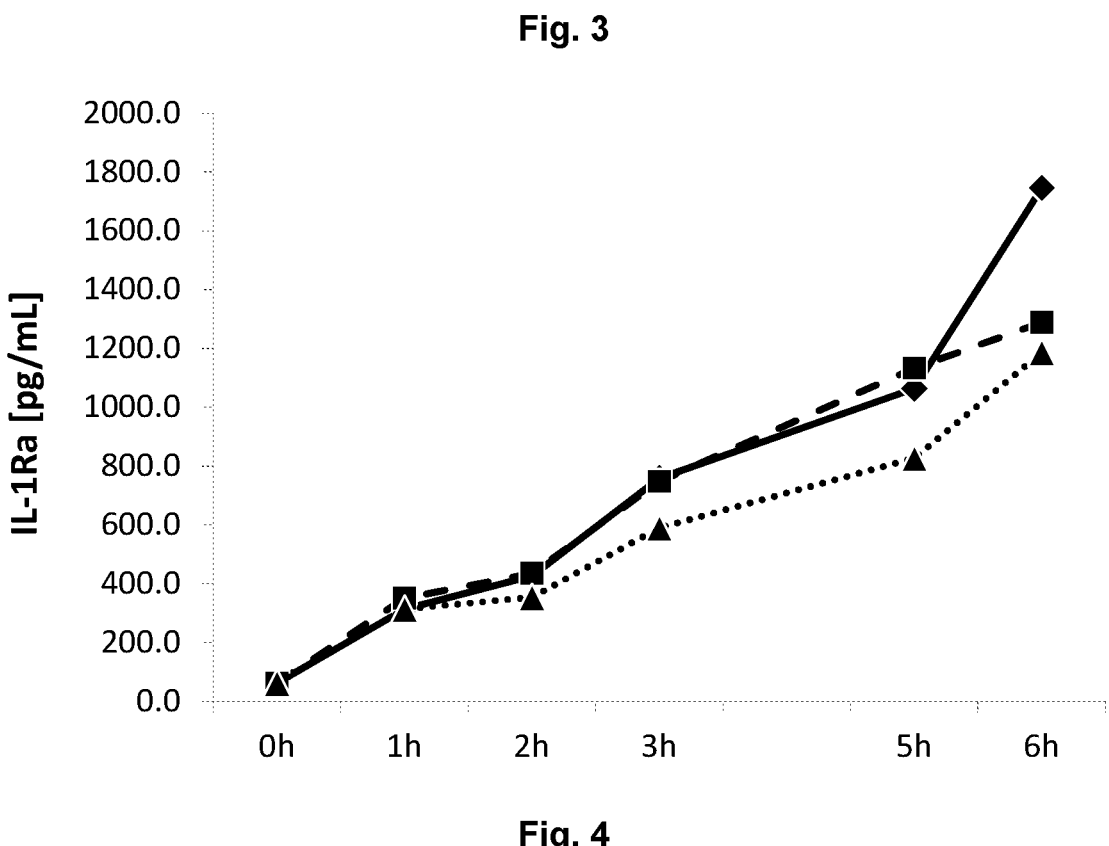
FIG. 3 shows the time course of the concentration of IL-1Ra under three different conditions (x-axis: time of incubation in hours; y-axis: concentration of IL-1Ra in pg/ml).
Figure 4:
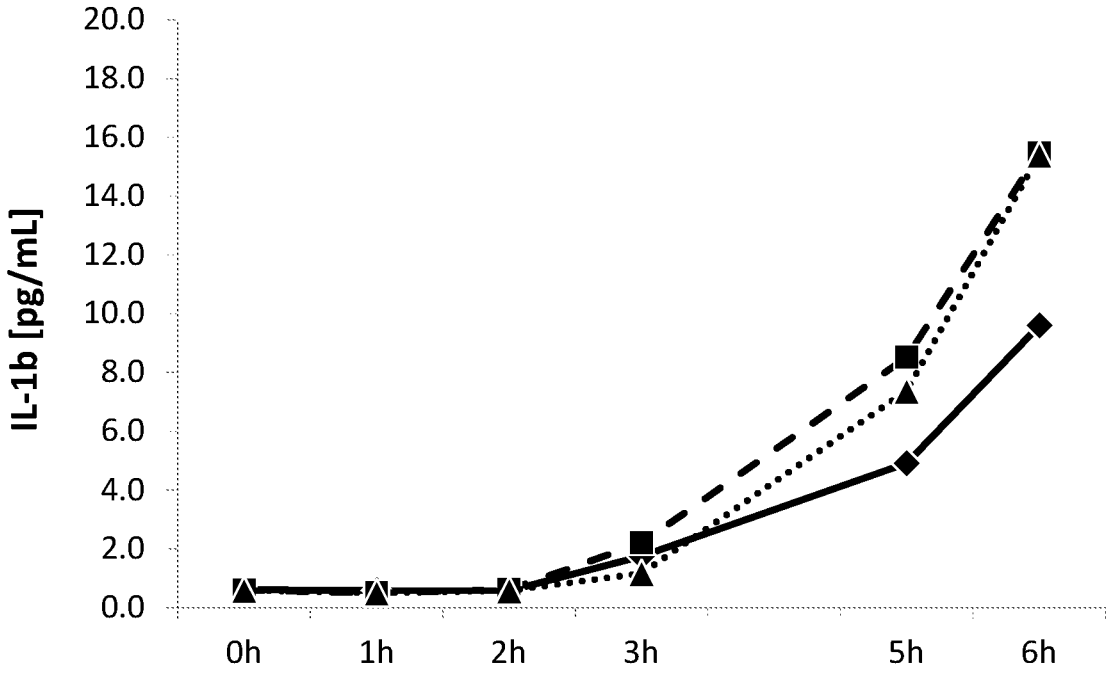
FIG. 4 shows the time course of the concentration of IL-1B under three different conditions (x-axis: time of incubation in hours; y-axis: concentration of IL-1B in pg/ml).

FIG. 2 shows the average ratio of IL-1Ra to IL-1β, FIG. 3 the average concentration of IL-1Ra and FIG. 4 the average concentration of IL-1β. The curves are: static incubation (triangle symbols, dotted line), incubation with fast shaking (square symbols, dashed line), incubation with slow rotation (diamond symbols, continuous line).

It can be seen that agitation leads to an increase in the concentration of IL-1Ra. In contrast, the concentration of IL-1β was about the same with and without agitation, or even lower in the case of slow rotation. Agitation is thus able to lead to an increase in the ratio of IL-1Ra to IL-1β, which is particularly pronounced in the case of slow rotation. It needs to be kept in mind that the calculated ratios are more prone to error if the IL-1β levels are very low, because such concentrations can be measured less accurately.

Table 2 indicates the measured ratios of IL-1Ra to IL-1β, Table 3 the measured concentrations of IL-1Ra and Table 4 the measured concentrations of IL-1β. Incubation was performed as static incubation, with fast shaking or with slow rotation as defined above.

TABLE 2

Ratios of the IL-1Ra concentration to the IL-1β concentration measured after the indicated incubation times (see FIG. 2).

|  | 0 h | 1 h | 2 h | 3 h | 5 h | 6 h |
|---|---|---|---|---|---|---|
| Slow rotation | 102.3 | 582.4 | 793.2 | 808.0 | 274.4 | 262.4 |
| Fast shaking |  | 692.9 | 769.2 | 658.8 | 141.5 | 105.3 |
| Static incubation |  | 627.8 | 658.9 | 571.0 | 123.7 | 80.0 |

TABLE 3 TABLE 3

IL-1Ra concentrations in pg/ml measured after the indicated incubation times (see FIG. 3).

|  | 0 h | 1 h | 2 h | 3 h | 5 h | 6 h |
|---|---|---|---|---|---|---|
| Slow rotation | 61.9 | 313.3 | 425.9 | 758.6 | 1064.1 | 1746.1 |
| Fast shaking |  | 350.7 | 436.0 | 747.8 | 1133.7 | 1288.7 |
| Static incubation |  | 313.9 | 353.5 | 590.1 | 827.8 | 1186.5 |

TABLE 4

IL-1β concentrations in pg/ml measured after the indicated incubation times (see FIG. 4)

|  | 0 h | 1 h | 2 h | 3 h | 5 h | 6 h |
|---|---|---|---|---|---|---|
| Slow rotation | 0.6 | 0.6 | 0.6 | 1.8 | 4.9 | 9.6 |
| Fast shaking |  | 0.5 | 0.6 | 2.2 | 8.5 | 15.5 |
| Static incubation |  | 0.5 | 0.6 | 1.2 | 7.4 | 15.4 |

To sum up, it was confirmed that agitation improves the level of the desired factor IL-1Ra without adversely affecting, or favourably affecting, the level of the undesired factor IL-1β. As apparent in particular from the concentration ratio of IL-1Ra to IL-1β, according to the present invention pharmaceutical agents may be produced are even more valuable as an anti-inflammatory agent than those produced using static incubation according to the prior art.

Example 3: Increased Production of Resolvin D1 Due to Various Modes of Agitation Certain metabolites (oxylipins) derived from eicosapentaenoic acid (20:5(n-3), also referred to as "EPA"), docosapentaenoic acid (22:5(n-3)) and especially docosahexaenoic acid (22:6(n-3), also referred to as "DHA") and termed the (neuro) protectins, resolvins and maresins have potent anti-inflammatory and immunoregulatory actions at concentrations in the nanomolar and picomolar range. Resolvin D1, which is a mediator of self-limited resolution of inflammation, was evaluated as an example of such biologically active polyunsaturated fatty acid metabolites. It leads to a suppression of TNF-α expression. Resolvins are also potent analgesics for arthritic and neuropathic pain.

A pharmaceutical agent was produced by the method of the present invention as follows:

Peripheral whole blood was collected from four healthy human beings. Blood was drawn into glass beads-containing syringes as described in Example 1.

The syringes containing the samples were incubated at 37° C. in a Sanyo MCO-20AIC incubator (Japan) without addition of $CO_2$.

One part of the samples was incubated without agitation (static incubation).

Another part of the samples was agitated during incubation by fast shaking as defined in Example 2.

Yet another part of the samples was agitated during incubation by slow rotation as defined in Example 1.

After incubation, insoluble components were removed by centrifugation. The resulting conditioned serum was collected and examined by ELISA for the concentration of various factors, including resolvin D1.

Figure 5:
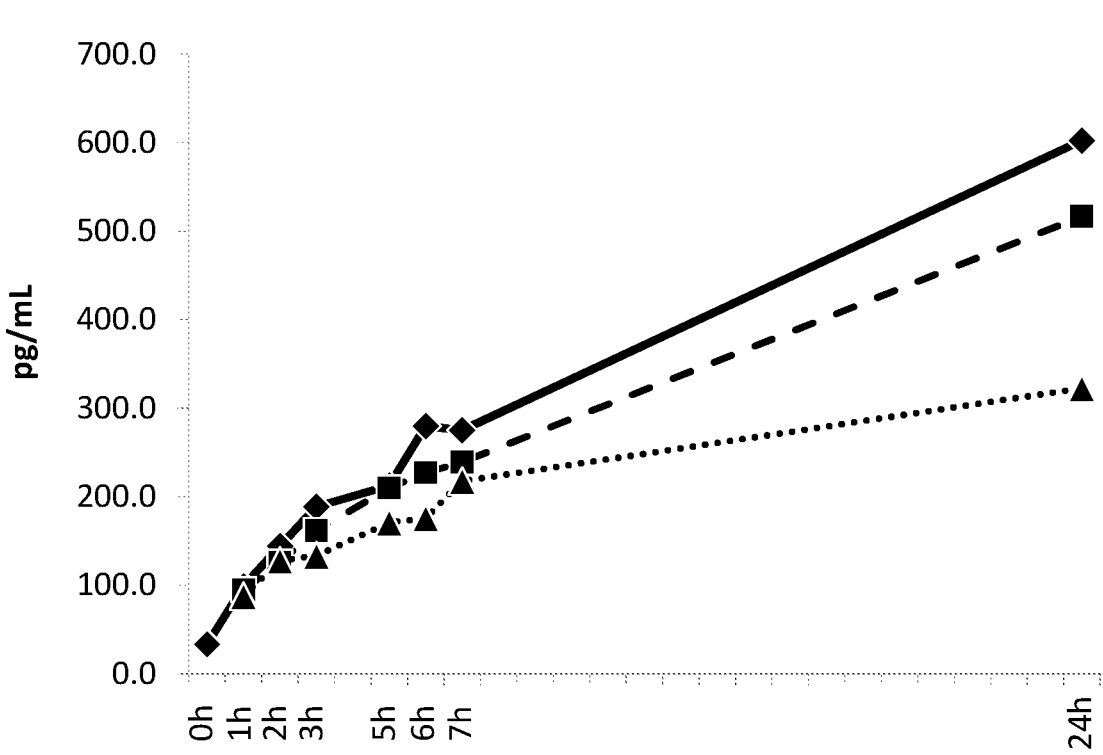
FIG. 5 shows the time course of the concentration of resolvin D1 under three different conditions (x-axis: time of incubation in hours; y-axis: concentration of resolvin D1 in pg/ml).

FIG. 5 shows the average concentrations of resolvin D1 over time. The following curves are depicted: static incubation (triangle symbols, dotted line), incubation with fast shaking (square symbols, dashed line), incubation with slow rotation (diamond symbols, continuous line).

It can be seen that incubation led to a time-dependent concentration increase. Agitation during incubation leads to a more pronounced increase than static incubation. The effect was even stronger with slow rotation than when the sample was agitated by fast shaking.

Table 5 indicates the measured concentrations. Incubation was performed as static incubation, with fast shaking or with slow rotation as defined above.

TABLE 5

Resolvin D1 concentrations in pg/ml measured
after the indicated incubation times.
The absence of incubation is designated referred to as 0 h.

| | 0 h | 1 h | 2 h | 3 h | 5 h | 6 h | 7 h | 24 h |
|---|---|---|---|---|---|---|---|---|
| Slow rotation | 33.0 | 98.9 | 144.0 | 188.5 | 212.3 | 279.8 | 275.0 | 602.2 |
| Fast shaking | | 94.7 | 125.9 | 161.6 | 209.8 | 226.9 | 238.8 | 516.4 |
| Static incubation | | 87.8 | 127.8 | 133.1 | 170.7 | 175.6 | 217.6 | 322.4 |

The concentrations of IL-5 and IFN-$\gamma$ were below the threshold of detection.

Consequently, agitation is able to lead to pharmaceutical agents that may be more efficacious in the resolution of inflammation, suppression of TNF-$\alpha$ expression and analgesia.

Example 4: Increased Production of Exosomes Due to Various Modes of Agitation

As mentioned above, exosomes are known in the treatment of a variety of conditions. Therefore, the therapeutic value of pharmaceutical agents which contains exosomes may be expected to be dependent on the concentration of exosomes.

In the same experiment as described in Example 3, also the concentration of exosomes was examined by ELISA.

Figure 6:
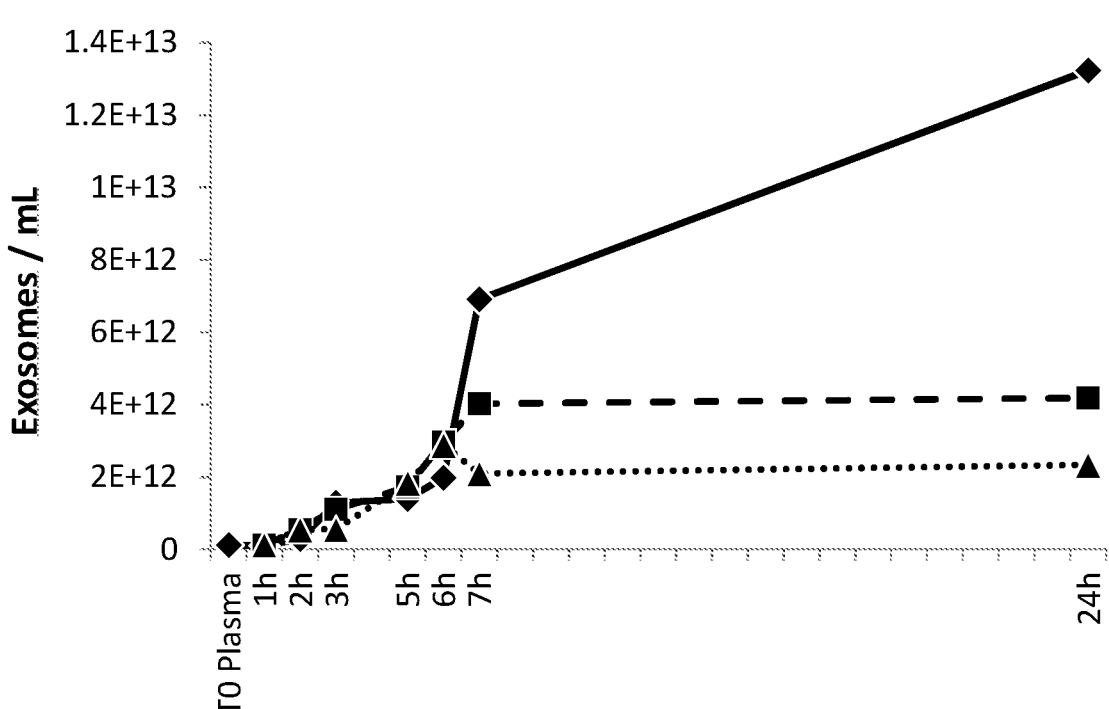
FIG. 6 shows the time course of the concentration of exosomes under three different conditions (x-axis: time of incubation in hours, wherein T0 designates the absence of incubation; y-axis: concentration of exosomes, expressed as exosome count per ml).

FIG. 6 shows the average concentrations of exosomes over time. The following curves are depicted: static incubation (triangle symbols, dotted line), incubation with fast shaking (square symbols, dashed line), incubation with slow rotation (diamond symbols, continuous line).

It is apparent that incubation led to a time-dependent exosome concentration increase. Agitation is able to increase the concentration of exosomes even further.

Table 6 indicates the measured concentrations. Incubation was performed as static incubation, with fast shaking or with slow rotation as defined above.

TABLE 6

Exosome concentrations in exosomes/ml measured after the
indicated incubation times. The absence of
incubation is referred to as 0 h (T0 in FIG. 6).

TABLE 6-continued

| | 0 h | 1 h | 2 h | 3 h |
|---|---|---|---|---|
| Slow rotation | 1.164E+11 | 9.94E+10 | 2.867E+11 | 1.2864E+12 |
| Fast shaking | | 1.281E+11 | 5.399E+11 | 1.1099E+12 |
| Static incubation | | 1.391E+11 | 5.509E+11 | 5.553E+11 |

| | 5 h | 6 h | 7 h | 24 h |
|---|---|---|---|---|
| Slow rotation | 1.4008E+12 | 1.9829E+12 | 6.9129E+12 | 1.32379E+13 |
| Fast shaking | 1.7237E+12 | 2.9724E+12 | 4.0241E+12 | 4.1858E+12 |
| Static incubation | 1.8395E+12 | 2.8878E+12 | 2.0937E+12 | 2.3345E+12 |

This means that according to the present invention pharmaceutical agents may be produced that have increased in value in the treatment of the above mentioned conditions.

Example 5: Increased Production of Gelsolin Due to Various Modes of Agitation

Gelsolin can inhibit apoptosis by stabilising mitochondria. More specifically, it inhibits the release of cytochrome C and thus impedes a signal amplification cascade leading to apoptosis. It is further an actin-binding (capping) protein that also aids in actin polymerisation.

In the same experiment as described in Example 3, also the concentration of gelsolin was examined by ELISA.

Figure 7:
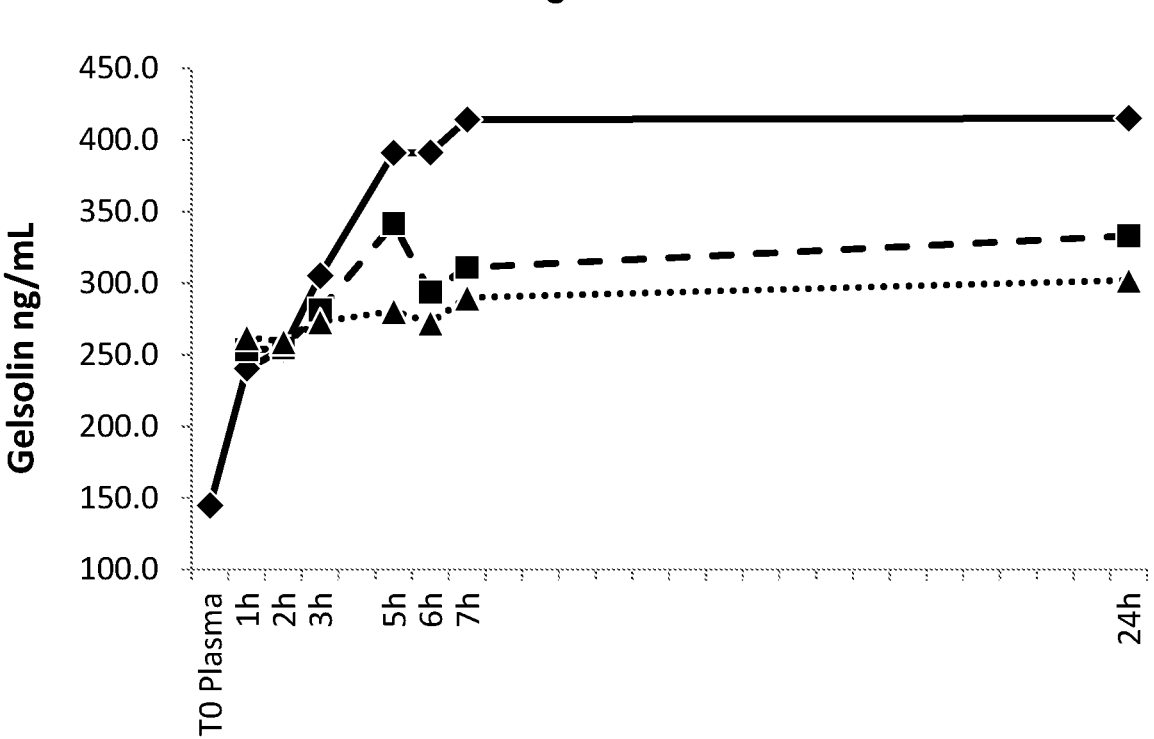
FIG. 7 shows the time course of the concentration of gelsolin under three different conditions (x-axis: time of incubation in hours, wherein T0 designates the absence of incubation; y-axis: concentration of gelsolin in ng/ml).

FIG. 7 shows the average concentrations of gelsolin over time. The following curves are depicted: static incubation (triangle symbols, dotted line), incubation with fast shaking (square symbols, dashed line), incubation with slow rotation (diamond symbols, continuous line).

It was found that incubation led to a time-dependent increase of gelsolin concentration. Agitation is able to increase gelsolin concentration even further.

Table 7 indicates the measured concentrations. Incubation was performed as static incubation, with fast shaking or with slow rotation as defined above.

TABLE 7

Gelsolin concentrations in ng/ml measured after
the indicated incubation times. The
absence of incubation is referred to as 0 h (T0 in FIG. 7).

| | 0 h | 1 h | 2 h | 3 h | 5 h | 6 h | 7 h | 24 h |
|---|---|---|---|---|---|---|---|---|
| Slow rotation | 144.8 | 240.5 | 253.7 | 305.3 | 390.9 | 391.2 | 414.2 | 415.2 |
| Fast shaking | | 253.5 | 254.7 | 281.1 | 341.5 | 293.8 | 310.9 | 333.0 |
| Static incubation | | 262.3 | 259.3 | 273.2 | 280.5 | 272.5 | 289.9 | 302.0 |

Consequently, the present invention allows the production of pharmaceutical agents with increased efficacy in the inhibition of apoptosis. This has implications for conditions in which apoptosis plays a role.

Example 6: Differential Production of IL-1Ra Due to Agitation During Incubation, Three Test Subjects A pharmaceutical agent was produced by the method of the present invention as follows:

Peripheral whole blood was collected from four healthy human beings. Blood was drawn into pyrogen-free 10 ml plastic syringes (interior length: ca. 84.5 mm, interior diameter: ca. 14.3 mm, interior surface: ca. 4100 mm², interior volume: ca. 13500 mm³), which neither contained glass beads nor contained any other particles for contacting the liquid.

The syringes containing the samples were incubated for various incubation times at 37° C. in a Sanyo MCO-20AIC incubator (Japan) without addition of $CO_2$.

One part of the samples was incubated without agitation (static incubation).

Another part of the samples was agitated during incubation by fast shaking as defined in Example 2.

Yet another part of the samples was agitated during incubation by slow rotation as defined in Example 1.

After incubation, insoluble components were removed by centrifugation. The resulting conditioned serum was collected and examined by ELISA for the concentrations of IL-1Ra.

Figure 8:
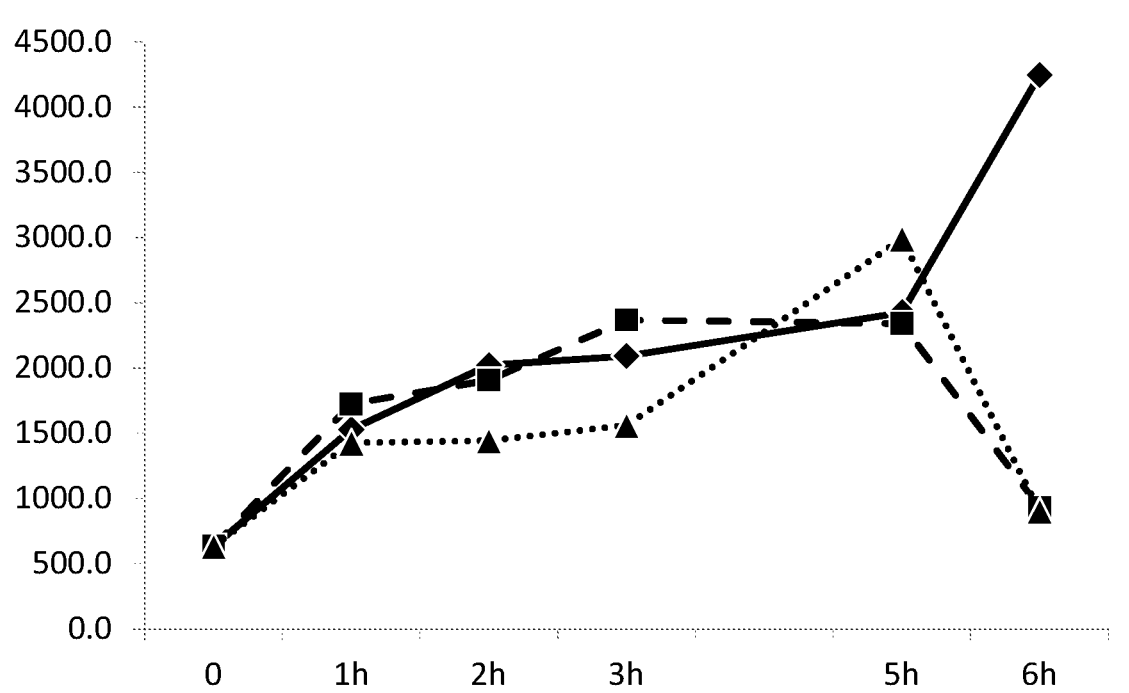
FIG. 8 shows the time course of the concentration ratio of IL-1Ra to IL-1β under three different conditions (x-axis: time of incubation in hours; y-axis: ratio of the concentrations of IL-1Ra and IL-1β, both in pg/ml).
Figure 9:
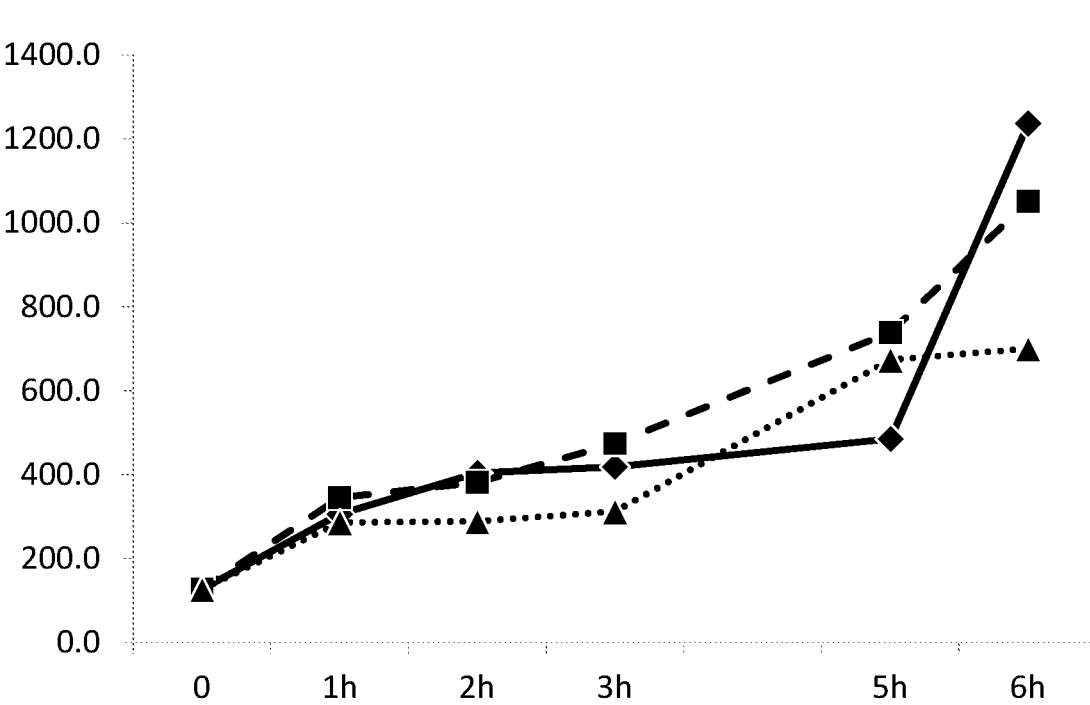
FIG. 9 shows the time course of the concentration of IL-1Ra under three different conditions (x-axis: time of incubation in hours; y-axis: concentration of IL-1Ra in pg/ml).
Figure 10:
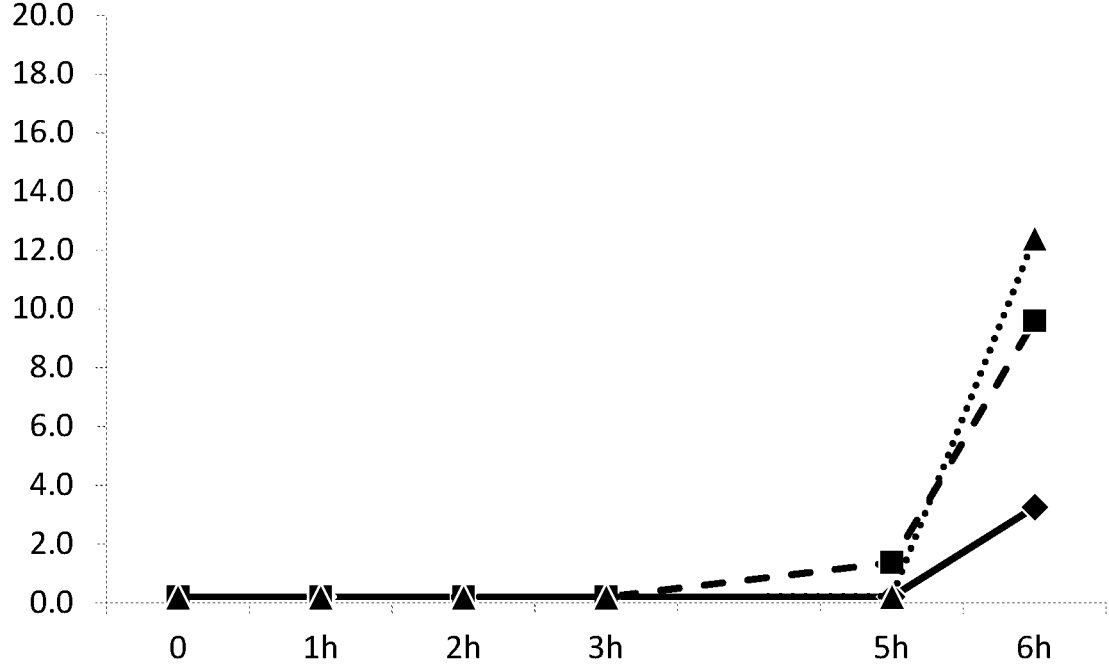
FIG. 10 shows the time course of the concentration of IL-1β under three different conditions (x-axis: time of incubation in hours; y-axis: concentration of IL-1β in pg/ml).

FIG. 8 shows the average ratio of IL-1Ra to IL-1β, FIG. 9 the average concentration of IL-1Ra and FIG. 10 the average concentration of IL-1β. The curves are: static incubation (triangle symbols, dotted line), incubation with fast shaking (square symbols, dashed line), incubation with slow rotation (diamond symbols, continuous line).

It can be seen that also in the absence of particles for contacting the liquid, agitation leads to an increase in the concentration of IL-1Ra.

In contrast, the concentration of IL-1β was about the same with and without agitation, or even lower in the case of slow rotation. Also in the absence of particles, and potentially depending on incubation time, agitation is thus able to lead to an increase in the ratio of IL-1Ra to IL-1β, which may be particularly pronounced in the case of slow rotation. It needs to be kept in mind that the calculated ratios are more prone to error if the IL-13 levels are very low, because such concentrations can be measured less accurately.

Table 8 indicates the measured ratios of IL-1Ra to IL-1β, Table 3 the measured concentrations of IL-1Ra and Table 4 the measured concentrations of IL-1β. Incubation was performed as static incubation, with fast shaking or with slow rotation as defined above.

TABLE 8

Ratios of the IL-1Ra concentration to the IL-1β concentration measured after the indicated incubation times (see FIG. 8).

| | 0 h | 1 h | 2 h | 3 h | 5 h | 6 h |
|---|---|---|---|---|---|---|
| Slow rotation | 633.9 | 1529.6 | 2022.0 | 2091.0 | 2426.2 | 4244.3 |
| Fast shaking | | 1725.1 | 1906.2 | 2367.5 | 2340.9 | 930.2 |
| Static incubation | | 1428.1 | 1442.5 | 1560.2 | 2989.2 | 904.1 |

TABLE 9

IL-1Ra concentrations in pg/ml measured after the indicated incubation times (see FIG. 9).

| | 0 h | 1 h | 2 h | 3 h | 5 h | 6 h |
|---|---|---|---|---|---|---|
| Slow rotation | 126.8 | 305.9 | 404.4 | 418.2 | 485.2 | 1236.1 |
| Fast shaking | | 345.0 | 381.2 | 473.5 | 738.9 | 1050.8 |
| Static incubation | | 285.6 | 288.5 | 312.0 | 673.9 | 700.3 |

TABLE 10

IL-1β concentrations in pg/ml measured after the indicated incubation times (see FIG. 10).

| | 0 h | 1 h | 2 h | 3 h | 5 h | 6 h |
|---|---|---|---|---|---|---|
| Slow rotation | 0.2 | 0.2 | 0.2 | 0.2 | 0.2 | 3.3 |
| Fast shaking | | 0.2 | 0.2 | 0.2 | 1.4 | 9.6 |
| Static incubation | | 0.2 | 0.2 | 0.2 | 0.2 | 12.4 |

Agitation improves the level of the desired factor IL-1Ra also in the absence of glass beads or other particles. As compared with their presence, the levels of IL-1Ra are somewhat lower, consistent with the explanation that such particles increase the surface for contacting the liquid and improve induction. Excellent ratios of IL-1Ra to IL-1β and low levels of IL-1β may also be achieved in the absence of particles.

The invention claimed is:

1. A method for producing a pharmaceutical composition, comprising the steps of:
   (a) providing a liquid collected from a mammal, which liquid comprises cellular constituents of blood,
   (b) providing a container having an internal surface,
   (c) contacting said liquid with said internal surface,
   (d) incubating said liquid contacted with said internal surface for an incubation time of at least 3 hours, wherein said liquid is agitated with an agitation means at least once during said incubation time, wherein said liquid is agitated for a total of at least 1 hour, wherein by agitating the liquid, the liquid is mixed, and
   (e) after said incubation time has passed, obtaining said pharmaceutical composition by steps comprising (1) collecting said liquid or (2) removing part of or the entirety of said cellular constituents from said liquid and collecting the remainder,
   wherein in said pharmaceutical composition, the concentration of IL-1Ra is higher than in the absence of agitation under otherwise identical conditions.

2. The method according to claim 1, wherein said container:
   contains particles for contacting said liquid, which are one or more selected from macroscopic particles, microscopic particles and nanoparticles,
   has an internal surface that comprises a surface made of one or more selected from glass, plastic, corundum and quartz, or
   has a volume of 1 ml to 1000 ml.

3. The method according to claim 1, wherein said liquid is a blood sample, preferably a whole blood sample or a whole blood sample from which erythrocytes have been depleted.

4. The method according to claim 1, wherein said liquid is
   (1) agitated during the entirety of said incubation time,
   (2) agitated two or more times during said incubation time,
   (3) agitated at a point in time that is later than 10 minutes after the beginning of said incubation time,
   (4) not agitated during the first 10 minutes of the incubation time, or
   (5) agitated by one or more selected from: rotating the container around an axis thereof, moving an axis of the container along a closed trajectory, shifting the container, tilting the container, inverting the container, shaking the container, rotating the liquid, shifting the liquid and stirring the liquid.

5. The method according to claim 1, wherein said agitation means is selected from a wheel-shaped or propeller-shaped device for rotating the container around an axis thereof, wherein preferably the device has a rotation axis that is perpendicular to the direction of gravity or tilted by an angle of up to 90 degrees, and a shaking device, which is preferably adapted to carry out a circular or translational motion.

6. The method according to claim 1, wherein said incubation is performed under one or more of the following conditions:

for an incubation time of 3 hours to 5 hours, 3 hours to less than 24 hours, 3 hours to 20 hours, 3 hours to 16 hours, 4 hours to 12 hours, at least 5 hours, 5 hours to 10 hours, 5 hours to 7 hours, up to 6 hours, at least 6 hours or at least 7 hours, at a temperature from 30° C. to 40° C., preferably at 37° C., or in the absence or presence of an added anticoagulant.

7. The method according to claim 1, wherein in said pharmaceutical composition the concentration of exosomes is higher than in the absence of agitation under otherwise identical conditions, preferably at least 1.1-fold as high, the concentration of gelsolin is higher than in the absence of agitation under otherwise identical conditions, preferably at least 1.1-fold as high, the concentration of resolvin is higher than in the absence of agitation under otherwise identical conditions, preferably at least 1.1-fold as high, at least one ratio of the concentrations of an anti-inflammatory mediator (preferably IL-1Ra) and an inflammatory mediator (preferably IL-1β) is higher than in the absence of agitation under otherwise identical conditions, preferably at least 1.1-fold as high, or at least one concentration of an inflammatory mediator (preferably IL-5 or IFN-γ) is essentially the same as before said incubation.

8. The method according to claim 1, wherein said cellular constituents of blood comprise platelets and step (e) is a step of, after said incubation time has passed, obtaining said pharmaceutical composition by degranulating said platelets by adding calcium ions and/or thrombin, and thereafter collecting said liquid.

9. The method according to claim 1, wherein said liquid is agitated during the entirety of said incubation time.

10. The method according to claim 1, wherein said liquid is agitated two or more times during said incubation time.

11. The method according to claim 1, wherein said liquid is agitated by one or more selected from: rotating the container around an axis thereof, moving an axis of the container along a closed trajectory, shifting the container, tilting the container, inverting the container, shaking the container, rotating the liquid, shifting the liquid and stirring the liquid.

12. The method according to claim 1, wherein said agitation means is a wheel-shaped or propeller-shaped device for rotating the container around an axis thereof.

13. The method according to claim 1, wherein said agitation means is a shaking device.

14. The method according to claim 1, wherein the mammal is a human being.

15. The method according to claim 1, wherein the concentration of IL-1Ra is at least 1.1-fold as high as that in the absence of agitation under otherwise identical conditions.

* * * * *